United States Patent [19]
Yazaki et al.

[11] Patent Number: 5,063,061
[45] Date of Patent: Nov. 5, 1991

[54] AQUEOUS PREPARATION OF PYRIDO(1,2-A)PYRIMIDINE COMPOUND

[75] Inventors: Takashi Yazaki, Misato; Tomohisa Matsushita, Okegawa; Tsutomu Nagase, Ohizumimachi, all of Japan

[73] Assignee: Tokyo Tanabe Company, Tokyo, Japan

[21] Appl. No.: 499,954

[22] Filed: Mar. 27, 1990

[30] Foreign Application Priority Data

Jun. 9, 1989 [JP] Japan .................................. 1-145201

[51] Int. Cl.$^5$ ........................ A61F 2/00; A61F 13/00; A61K 31/52
[52] U.S. Cl. .................................. 424/427; 424/434; 514/258; 514/912
[58] Field of Search ................ 424/427, 434; 514/913, 514/258, 912

[56] References Cited

U.S. PATENT DOCUMENTS

| 4,425,344 | 1/1984 | Horlington | 514/913 |
| 4,425,345 | 11/1984 | Horlington | 514/913 |
| 4,798,832 | 11/1989 | Matsuishi | 514/258 |
| 4,816,459 | 3/1989 | Matsuishi | 514/528 |

Primary Examiner—Thurman K. Page
Assistant Examiner—G. S. Kishore
Attorney, Agent, or Firm—McGlew & Tuttle

[57] ABSTRACT

An aqueous preparation comprising of 0.1 to 0.3% (W/V) of a pyrido[1,2-a]pyrimidine compound represented by the following formula:

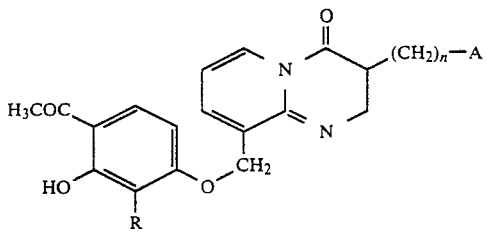

wherein R represents an n-propyl or allyl group, A represents a tetrazolyl or carboxyl group, and n represents an integer of 0 to 2, 0.5 to 2.0% (W/V) of a polyoxyethylene sorbitan fatty acid ester, 0.5 to 2.0% (W/V) of polyethylene glycol and 1.0 to 3.5% (W/V) of disodium hydrogenphosphate.

7 Claims, No Drawings

AQUEOUS PREPARATION OF PYRIDO(1,2-A)PYRIMIDINE COMPOUND

BACKGROUND OF THE INVENTION

1. Field of the Invention

This invention relates to an aqueous preparation of an anti-allergic drug, and specifically, to an aqueous preparation, particularly an eye drop, a nasal drop or a paint, comprising a pyrido[1,2-a]pyrimidine compound.

2. Description of the Prior Art

Pyrido[1,2-a]pyrimidine compounds are described in Japanese Laid-Open Patent Publication Nos. 242682/1987, 183581/1988 and 246375/1988 and are known to have a strong action of inhibiting Leukotriene $D_4$ which is a typical active substance of a slow reacting substance of anaphylaxis (SRS-A) and to suppress or prevent conditions of allergic reactions such as SRS-A induced I-type allergic rhinitis.

SUMMARY OF THE INVENTION

Anti-allergic agents now on the market are mainly for oral administration designed for systemic action. However, orally administrable agents are not necessarily a suitable form of administration for patients of allergic ophthalmia, rhinitis or dermatitis, particularly infants and young children, because of their side-effects. Accordingly, to reduce side-effects and efficiently produce a pharmacological efficacy, an effective form of administration would be a local therapeutic agent, for example, an eye drop for allergic ophthalmia, a nasal drop for allergic rhinitis and a paint for allergic dermatitis.

It is an object of this invention to provide an aqueous preparation, such as an eye drop, a nasal drop or a paint, of a pyrido[1,2-a]pyrimidine compound, an anti-allergic agent.

The aqueous preparation should meet certain requirements. For example, it should be in the form of an aqueous solution. It should be germ-free. It should not contain foreign matter. The tonicity and pH value of the agent should not be much different from those of a body fluid at the site of application. It should not irritate the sites of application, for example, the mucosa of the eye, the mucosa of the nose, or the skin. Furthermore, it should be physically and chemically stable during longterm storage.

Generally, the pyrido[1,2-a]pyrimidine compound has a low solubility in water. For example, 9-[(4-acetyl-3-hydroxy-2-n-propylphenoxy)methyl]-3-(1H-tetrazol-5-yl)-4H-pyrido[1,2-a]pyrimidin-4-one (to be referred to as AS-35) has a solubility in water of 0.4 ug/ml. To prepare an aqueous preparation of the pyrido[1,2-a]pyrimidine compound, it is necessary to dissolve it in concentrations within a range in which its pharmacological efficacy is exhibited, and to prevent precipitation of crystals after dissolution. For example, when a 1N sodium hydroxide solution was used, a clear solution was formed at an AS-35 concentration of 0.1% to 0.2% (W/V). But because this solution had a pH of as high as 11 and became gel-like, it was unsuitable as the aqueous preparation. When an aqueous solution of citric acid was added to adjust its pH to 8.4 which is close to the pH of a body fluid, crystals precipitated on the next day. Furthermore, to dissolve AS-35, a dissolving adjuvant such as polyoxyethylene hydrogenated castor oil, a polyoxyethylene sorbitan fatty acid ester, polyoxyl 40 stearate, polyethylene glycol, glycerol, 2-octyldodecanol, diisopropanolamine, triethanolamine, trisaminomethane, meglumine or diethanolamine was added, AS-35 could not be dissolved with any of these adjuvants. When the Palitzsch's buffer solution and the Gifford's buffer solution known as opthalmic buffer solution [Japanese-language publication, "*Shin Yakuzaigaku Soron*" (Nankodo), 1980 edition, page 39–42] are used, AS-35 was not dissolved.

Furthermore, [9-(4-acetyl-3-hydroxy-2-n-propylphenoxymethyl)-4-oxo-pyrido[1,2-a]pyrimidin-3-yl]acetic acid (to be referred to as AS-148) and 9-[(4-acetyl-3-hydroxy-2-n-propylphenoxy)methyl]-3-[2-(1H-tetrazol-5-yl)ethyl]-4H-pyrido[1,2-a]pyrimidin-4-one (to be referred to as AS-163) could not be formed into an aqueous solution as AS-35 could not. The present inventors confirmed the above finding by their own experiments.

Since it is anticipated that other pyrido[1,2-a]pyrimidine compounds will show the same behaviors as AS-35, AS-148 and AS-163, the above method would not be able to give aqueous preparations of the pyrido[1,2-a]pyrimidine compounds.

In view of the above-mentioned situation, the present inventors made extensive investigations on aqueous preparations of the pyrido[1,2-a]pyrimidine compounds. These investigations led to the discovery that by adding a polyoxyethylene sorbitan fatty acid ester (to be referred to as polysorbate), polyethylene glycol (to be referred to as PEG) and disodium hydrogenphosphate, pyrido[1,2-a]pyrimidine compounds can be dissolved in water in high concentrations; on longterm storage of the aqueous preparations, crystals do not precipitate and the pyrido[1,2-a]pyrimidine compounds do not undergo decomposition; and that the aqueous preparations have no local irritation. The present invention has been accomplished on the basis of this discovery.

Thus, the present invention provides an aqueous preparation comprising 0.1 to 0.3% (W/V) of a pyrido[1,2-a]pyrimidine compound represented by the following formula:

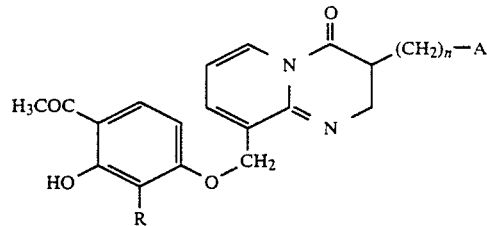

wherein R represents an n-propyl or allyl group, A represents a tetrazolyl or carboxyl group, and n represents an integer of 0 to 2, 0.5 to 2.0% (W/V) of a polyoxyethylene sorbitan fatty acid ester, 0.5 to 2.0% (W/V) of polyethylene glycol and 1.0 to 3.5% (W/V) of disodium hydrogenphosphate.

DETAILED DESCRIPTION OF THE PREFERRED EMBODIMENTS

Examples of the pyrido[1,2-a]pyrimidine compounds include 3-[9-(4-acetyl-3-hydroxy-2-n-propylphenoxymethyl)-4-oxo-pyrido[1,2-a]pyrimidin-3-yl]propionic acid (to be referred to as AS-152), 9-[(4-acetyl-3-hydroxy-2-n-propylphenoxy)methyl]-3-[(1H-tetrazol-5-yl)methyl]-4H-pyrido[1,2-a]pyrimidin-4-one (to be referred to as AS-174) and 9-[(4-acetyl-3-hydroxy-2-allylphenoxy)methyl]-3-(1H-tetrazol-5-yl)-4H-pyrido[1,2-a]pyrimidin-4-one (to be referred to as AS-168) in addition to AS-35, AS-148 and AS-163. In the following, AS-148 and AS-152 will be generically called the carboxylic acid type, and AS-35, AS-163, AS-174 and AS-168, the tetrazole type.

Examples of the polysorbate include polyoxyethylene sorbitan monopalmitate (to be referred to as polysorbate 40), polyoxyethylene sorbitan monostearate (to be referred to as polysorbate 60), polyoxyethylene sorbitan tristearate (to be referred to as polysorbate 65), and polyoxyethylene sorbitan monooleate (to be referred to as polysorbate 80).

Examples of PEG include polyethylene glycol 200 (to be referred to as PEG 200), polyethylene glycol 300 (to be referred to as PEG 300), polyethylene glycol 400 (to be referred to as PEG 400), polyethylene glycol 600 (to be referred to as PEG 600), polyethylene glycol 1000 (to be referred to as PEG 1000), polyethylene glycol 1500 (to be referred to as PEG 1500), polyethylene glycol 1540 (to be referred to as PEG 1540), polyethylene glycol 4000 (to be referred to as PEG 4000), polyethylene glycol 6000 (to be referred to as PEG 6000), polyethylene glycol 20000 (to be referred to as PEG 20000).

As required, an antiseptic such as parahydroxybenzoic acid ester, benzethonium chloride, sodium dehydroacetate, chlorobutanol, phenylethyl alcohol or potassium sorbate, or an isotonizing agent such as sodium chloride, potassium chloride, sodium citrate or sodium acetate may be added to the aqueous preparation of this invention. The aqueous preparation of this invention is suitable as an eye drop, a nasal drop and a paint, and may also be utilized in a liquid preparation such as an injectable solution, an inhalant or an ear drop.

To permit use at room temperature as well as in a cold climate during the wintertime, the aqueous preparation of this invention does not precipitate crystals nor does the decomposition of the pyrido[1,2-a]pyrimidine compound occurs even when it is allowed to stand in a cold place for a long period of time. Thus, this aqueous preparation has quite excellent storage stability. Furthermore, the aqueous preparation of this invention is suitable as an eye drop, a nasal drop and a paint because it has a pH stabilized within a range of 8.3 to 8.4, is free from irritation of the mucosa of the eye and nose and also free from skin irritation, and remains stable even when allowed to stand in an open state.

Now, experiments were conducted on AS-35 and AS-163 selected as the tetrazole-type and AS-148 selected as the carboxylic acid-type by dissolving them in water using an alkali salt, the dissolving adjuvant, a known buffer solution, and a combination of these.

The solubility of crystals and the precipitation of crystals were evaluated by the visual inspection method described in the Japanese Pharmacopoeia. Specifically, samples are filled into tightly-stoppered glass container and allowed to stand. It was observed at a position having a brightness of 3000 to 5000 lux using a source of white light. When the crystals did not dissolve and when crystals precipitated, the results were rated as +. When the crystals dissolved and when precipitation of the crystals was not seen, the results were rated as −.

The sterile purified water mentioned hereinafter denotes water obtained by heat sterile purified water in an autoclave at 121° C. for 20 minutes.

When Alkali Salts were Used (1) When a 1N sodium hydroxide solution was used:
AS-35, AS-163 or AS-148 was suspended in sterile purified water to a concentration of 0.1% (W/V) or 0.2% (W/V), and a suitable amount of 1N sodium hydroxide solution was added in order to dissolve AS-35, AS-163 or AS-148. The solution was allowed to stand at room temperature. At any of the concentrations, AS-35, AS-163 or AS-148 dissolved, but the solutions has a pH of as high as 11.0 and became gel-like.

(2) When the pH was adjusted with citric acid:
An aqueous solution of citric acid was added to the above samples to adjust the pH to 8.4. When these samples were stored at room temperature, crystals precipitated at any of the concentrations at the time of preparation.

(3) When alkali salts were used:
To prepare a 0.2% (W/V) solution of AS-35, a 0.3% aqueous solution of each of various alkali salts in sterile purified water was added to AS-35 (0.2 g) to form 100 ml of a mixture. After well shaking, the resulting mixtures were allowed to stand at room temperature. The results are shown in the following table.

TABLE 1

| Alkali salt (3.0% (W/V)) | pH | Rating |
| --- | --- | --- |
| Sodium carbonate | 11.3 | − gel-like |
| Sodium hydrogencarbonate | 9.0 | + |
| Potassium carbonate | 11.5 | − gel-like |
| Potassium hydrogencarbonate | 9.0 | + |
| Sodium citrate | 8.1 | + |
| Disodium hydrogenphosphate | 8.7 | + |
| Dipotassium hydrogenphosphate | 8.6 | + |
| Borax | 9.3 | − gel-like |

When Dissolving Adjuvants were Added (1) When a surface-active agent was used:
Polyoxyl 40 stearate, polyoxyethylene hydrogenated castor oil or polysorbate 80 (5.0 g), as the surface-active agent, was heat-melted, and then 0.2 g or 0.1 g of AS-35 was added and uniformly dispersed. Then, sterile purified water was added to form 100 ml of a mixture. When the mixture was allowed to stand at room temperature, AS-35 was not dissolved in any of these cases. The same operation as above was repeated with regard to AS-163 and AS-148, but these compounds were not dissolved in any of these cases.

(2) When an organic amine-type dissolving adjuvant was added:
As the organic amine-type dissolving adjuvant, diisopropanolamine, triethanolamine, trisaminomethane, meglumine or diethanolamine (0.5 g) was dissolved in sterile purified water, and 0.2 g of AS-35 was added to form 100 ml of a mixture. In any case, AS-35 was not dissolved. When the same operation as above was repeated using AS-163 and AS-148, they were not dissolved in any of the cases.

(3) When other dissolving adjuvants were added:
0.5 g of 2-octyldodecanol, PEG-400 or glycerol wad dissolved in sterile purified water, and 0.1 g or 0.2 g of AS-35 was added to form 100 ml of a mixture. When it was well shaken and allowed to stand at room temperature, AS-35 was not dissolved in any of the cases. When the same operation was repeated with regard to AS-163 and AS-148, neither of them was dissolved in any of the cases.

When Known Buffer Solution was Used

When the Palitzsch's buffer solution or the Gifford's buffer solution was added to 0.2 g of AS-35 to form 100 ml of a mixture, and the mixture was well shaken and allowed to stand at room temperature, AS-35 was not dissolved in any of the cases. When the same operation was repeated with regard to AS-163 and AS-148, neither of them was dissolved in any of the cases.

When a Dissolving Adjuvant and a Buffer Solution were Used

AS-35 (0.2 g) and 2.0 g of polysorbate 80 and 2.0 g of PEG 400 were heat-melted, and under heat with stirring the Palitzsch's buffer solution or the Gifford's buffer solution was added to form 100 ml of a mixture. When it was well shaken and allowed to stand at room temperature, AS-35 was not dissolved in any of the cases.

The same operation as above was repeated with regard to AS-163 and AS-148. But these compounds were not dissolved in any of the cases.

When an Alkali Salt and a Dissolving Adjuvant were Used

AS-35, AS-163 or AS-148 (0.1 g) and polysorbate 80 (2.0 g) and PEG 400 (2.0 g) were mixed and uniformly dispersed, and a 3.0% (W/V) sterile purified water solution of an alkali salt was added to the dispersion to prepare 100 ml of a mixture. The mixture was shaken and allowed to stand at room temperature. The results are shown in the following table.

TABLE 2

| Alkali salt | AS-35 | | AS-163 | | AS-148 | |
|---|---|---|---|---|---|---|
| 3.0% (W/V) | pH | Rating | pH | Rating | pH | Rating |
| Sodium citrate | 7.9 | + | 7.7 | + | 7.8 | + |
| Sodium hydrogencarbonate | 8.5 | + | 8.6 | + | 8.5 | + |
| Potassium hydrogencarbonate | 8.7 | − | 8.8 | + | 8.9 | + |
| Borax | 9.7 | − | 9.5 | − | 9.5 | − |
| Sodium carbonate | 11.8 | − | 11.7 | − | 11.6 | − |
| Potassium carbonate | 12.0 | − | 12.0 | − | 11.9 | − |
| Dipotassium hydrogenphosphate | 8.9 | + | 8.6 | − | 8.8 | + |

As shown above, when an alkali salt, a known buffer solution and a dissolving adjuvant were added, individually, or in combination, to dissolve AS-35, AS-163 or AS-148, these compounds were not dissolved, or even when they dissolved, the resulting solution had a high pH or became gel-like. In any case, an aqueous preparation could not be formed.

The storage stability and the local irritation of the aqueous preparation of the invention are shown below.

Storage Stability (1) Storage in the tightly-stoppered state:

Predetermined amounts of AS-35, polysorbate 80 and PEG 400 were heat-melted, and with stirring, a heated solution of disodium hydrogenphosphate in sterile purified water was added. The mixture was cooled to room temperature. The resulting aqueous preparation was put in a tightly-stoppered glass container, and stored at room temperature or 5° C. The results are shown in Table 3. The evaluation at each of the times elapsed was carried out by the visual inspection method described hereinabove. Thin-layer chromatography (TLC) was carried out by using a silica gel thin-layer plate and a mixture of ethanol, toluene, acetone, aqueous ammonia and water (25:15:5:4:1) as a developing solution. The observations were terminated at the time when crystal precipitated, and TLC was taken at that time.

TABLE 3

| Sample | Concentration of AS-35 % (W/V) | Concentration of polysorbate 80 % (W/V) | Concentration of PEG 400 % (W/V) | Concentration of disodium hydrogenphosphate % (W/V) |
|---|---|---|---|---|
| 1 | 0.1 | 0.5 | 0.5 | 1.0 |
| 2 | 0.1 | 1.0 | 1.0 | 1.5 |
| 3 | 0.1 | 2.0 | 2.0 | 3.0 |
| 4 | 0.2 | 1.5 | 1.5 | 3.0 |
| 5 | 0.2 | 2.0 | 2.0 | 3.0 |
| 6 | 0.3 | 2.0 | 2.0 | 3.5 |

| Sample | pH* | Temperature | Rating At the beginning | Period of storage (months) 1 | 2 | 3 | 8 | TLC (number of spots) |
|---|---|---|---|---|---|---|---|---|
| 1 | 8.3 | 5° C. | − | − | − | + | | 1 |
| | | room temp. | − | − | − | − | | 1 |
| 2 | 8.4 | 5° C. | − | − | − | − | + | 1 |
| | | room temp. | − | − | − | − | − | 1 |
| 3 | 8.4 | 5° C. | − | − | − | − | − | 1 |
| | | room temp. | − | − | − | − | − | 1 |
| 4 | 8.4 | 5° C. | − | − | − | + | | 1 |
| | | room temp. | − | − | − | − | | 1 |
| 5 | 8.3 | 5° C. | − | − | − | − | − | 1 |
| | | room temp. | − | − | − | − | − | 1 |
| 6 | 8.3 | 5° C. | − | − | − | + | | 1 |
| | | room temp. | − | − | − | + | | 1 |

*The pH value showed no variation before and after the test.

Aqueous preparations containing 0.2% (W/V) of AS-35, 2.0% (W/V) of PEG 400, 3.0% (W/V) of disodium hydrogenphosphate and 2.0% (W/V) of polysorbate 40, polysorbate 60 or polysorbate 65 as the polysorbate as the polysorbate were prepared, placed in the tightly-stoppered glass and stored. Also, aqueous preparations containing 0.2% (W/V) of AS-35, 2.0% (W/V) of polysorbate 80, 3.0% (W/V) of disodium hydrogenphosphate and 2.0% (W/V) of PEG 200, PEG 300, PEG 400, PEG 600, PEG 1000, PEG 1500, PEG 1540, PEG 4000, PEG 6000, or PEG 20000 were prepared and stored at the temperatures indicated in Table 3 for 8 months in a tightly-stoppered state. These aqueous preparations were observed. No precipitation of crystals was noted, and no dissimilar spots were noted on TLC.

Aqueous preparations containing 2.0% (W/V) of polysorbate 80, 2.0% (W/V) of PEG, 3.0% (W/V) of disodium hydrogenphosphate and 0.2% (W/V) of AS-148, AS-152, AS-163, AS-174 or AS-168 as the pyrido[1,2-a]pyrimidine compound were prepared, and stored under the conditions shown in Table 3 for 8 months in a tightly-stoppered state. The stored preparations were observed, but no precipitation of crystals was noted. No dissimilar spots were noted on TLC.

(2) Storage in an open state:

The glass containers which contained samples 3 and 5 were opened after the lapse of 8 months, and these samples were stored at room temperature thereafter. No crystal precipitated after the lapse of 7 days, and no dissimilar spots were noted on TLC.

Local Irritation (1) Irritation to the ocular mucosa:

One drop of the eye drop of Example 1 was applied to the eye, and after the lapse of 30 minutes, the number of blinkings per minute was measured. Then the eye drop was applied 10 times at an interval of 30 minutes, and the irritation of the eye drop to the cornea, iris and conjunctiva was evaluated by the Draiz method (New Toxicity Testing Method-Method and Evaluation, page 337, Feb. 28, 1987, published by K. K. REALIZE). The results are shown in the following table.

TABLE 4

|  |  | Sample | Control |
|---|---|---|---|
| Number of blinkings |  | 4.0 | 3.7 |
| Irritation | Cornea | 0.0 | 0.0 |
|  | Iris | 0.0 | 0.0 |
|  | Conjunctiva | 4.0 | 4.0 |
|  | Total | 4.0 | 4.0 |

*Hardly any abnormality was noted in comparison with the control.

(2) Irritation of the nasal mucosa:

0.05 ml of the nasal drop of Example 2 was sprayed to the inside of the nasal cavity of rabbit for one week at a rate of 3 times a day. The epithelial tissues of the mucosa of the inside of the nasal cavity were observed under an optical microscope and an electron microscope. As compared with the control, no abnormality was noted.

(3) Irritation to the skin:

The paint of Example 3 (0.5 ml) was applied to the back of a rabbit for four days at a rate of two times a day, and then a skin irritation test was conducted on it by the Federal Register method (New toxicity Testing Method-Method and Evaluation page 336, Feb. 28, 1987, K. K. REALIZE). No abnormality was noted as compared with the control.

Advantage of the Invention

The aqueous preparations of the present invention, which are formulated so as to contain the pyrido[1,2-a]pyrimidine compound, polysorbate, polyethylene glycol and disodium hydrogenphospate in a concentration of 0.1–0.3% (W/V), 0.5–0.2% (W/V), 0.5–2.0% (W/V) and 1.0–3.5% (W/V), respectively, an aqueous preparation can be prepared in which the pyrido[1,2-a]pyrimidine compound, a difficultly-soluble drug, is dissolved in a high concentration to a suitable consistency at a pH close to the pH of a body fluid, crystals do not precipitate for a long period of time nor the pyrido[1,2-a]pyrimidine compound undergoes decomposition even when the preparation is stored at room temperature or in a cold place (5° C.), and which, moreover, does not cause local irritation. Furthermore, since the aqueous preparation of the invention is stable even in an open state, it is especially useful as an eye drop, a nasal drop and a paint which are used repeatedly with occasional opening of the container caps.

The following Examples illustrate the production of the aqueous preparation of this invention. It should be understood that the invention is not limited to these examples.

EXAMPLE 1

Formulation of an Eye Drop

Polysorbate 80 (20 g) and PEG 400 (20 g) were added to AS-35 (1.0 g) and uniformly dispersed. To the dispersion was added a solution of disodium hydrogenphosphate (30 g) and potassium sorbate (1.0 g) in sterile purified water. Sterile purified water was added further to give 1000 ml of a solution which had a pH of 8.3. This solution was filtered by using a 0.22 um membrane filter to give a 0.1% (W/V) solution of AS-35. The solution was filled in an eye drop container to produce an eye drop.

EXAMPLE 2

Formulation of a Nasal Drop

Polysorbate 80 (20 g) and PEG 400 (20 g) were added to AS-35 (1.0 g) and uniformly dispersed. To the dispersion was added a solution of disodium hydrogenphosphate (30 g) and potassium sorbate (1.0 g) in sterile purified water. Sterile purified water was further added to form 1000 ml of a solution having a pH of 8.3. This solution was filtered by using a 0.22 um membrane filter to form a 0.1% (W/V) solution of AS-35. The solution was filled in a spray-type nasal drop container to produce a nasal drop.

EXAMPLE 3

Formulation of a Paint

Polysorbate 80 (20 g) and PEG 400 (20 g) were added to AS-35 (2.0 g), and uniformly dispersed. To the dispersion was added a solution of disodium hydrogenphosphate (30 g) and sodium dehydroacetate (1.0 g) in sterile purified water, and sterile purified water was further added to form 1000 ml of a solution. The solution was filtered by using a 0.22 um membrane filter to give a 0.2% (W/V) solution of AS-35. This solution was filled in a plastic painting container with a sponge to produce a paint.

EXAMPLE 4

Formulation of an Eye Drop

Polysorbate 80 (20 g) and PEG 1500 (15 g) were added to AS-148 (1.0 g) and dispersed uniformly. To the dispersion was added a solution of disodium hydrogenphosphate (25 g) and potassium sorbate (1.0 g) in sterile purified water, and sterile purified water was further added to give 1000 ml of a solution. This solution was filtered through a 0.22 um membrane filter to form a 0.1% (W/V) solution of AS-148. This solution was filled in an eye drop container to produce an eye drop.

EXAMPLE 5

Formulation of a Nasal Drop

Polysorbate 65 (20 g) and PEG 4000 (15 g) were added to AS-148 (1.0 g) and uniformly dispersed. To the dispersion was added a solution of disodium hydrogenphosphate (30 g) and potassium sorbate (1.9 g) in sterile purified water. Sterile purified water was further added to form 1000 ml of a solution. This solution was filtered by using a 0.22 um membrane filter to form a 0.1% (W/V) solution of AS-148. The solution was filled in a spray-type nasal drop container to produce a nasal drop.

EXAMPLE 6

Formulation of a Paint

Polysorbate 80 (20 g) and PEG 4000 (20 g) were added to AS-148 (2.0 g), and uniformly dispersed. To the dispersion was added a solution of disodium hydrogenphosphate (30 g) and sodium dehydroacetate (1.0 g) in sterile purified water, and sterile purified water was further added to form 1000 ml of a solution. The solution was filtered by using a 0.22 um membrane filter to give a 0.2% (W/V) solution of AS-148. This solution was filled in a plastic painting container with a sponge to produce a paint.

EXAMPLE 7

Formulation of an Eye Drop

Polysorbate 65 (20 g) and PEG 4000 (15 g) were added to AS-163 (1.0 g) and dispersed uniformly. To the dispersion was added a solution of disodium hydrogenphosphate (25 g) and potassium sorbate (1.0 g) in sterile purified water, and sterile purified water was further added to give 1000 ml of a solution. This solution was filtered through a 0.22 um membrane filter to form a 0.1% (W/V) solution of AS-163. This solution was filled in an eye drop container to produce an eye drop.

EXAMPLE 8

Formulation of a Nasal Drop

Polysorbate 80 (15 g) and PEG 4000 (20 g) were added to AS-174 (1.0 g) and uniformly dispersed. To the dispersion was added a solution of disodium hydrogenphosphate (30 g) and potassium sorbate (1.0 g) in sterile purified water. Sterile purified water was further added to form 1000 ml of a solution. This solution was filtered by using a 0.22 um membrane filter to form a 0.1% (W/V) solution of AS-174. The solution was filled in a spray-type nasal drop container to produce a nasal drop.

EXAMPLE 9

Formulation of a Paint

Polysorbate 60 (20 g) and PEG 300 (20 g) were added to AS-168 (2.0 g) and uniformly dispersed. To the dispersion was added a solution of disodium hydrogenphosphate (35 g) and sodium dehydroacetate (1.0 g) in sterile purified water, and sterile purified water was further added to form 1000 ml of a solution. This solution was filtered through a 0.22 um membrane filter to form a 0.2% (W/V) of AS-168. The solution was filled in a plastic painting container with a sponge to produce a paint.

EXAMPLE 10

Formulation of an Eye Drop

Polysorbate 80 (20 g) and PEG 4000 (20 g) were added to AS-152 (1.0 g) and dispersed uniformly. To the dispersion was added a solution of disodium hydrogenphosphate (20 g) and potassium sorbate (1.0 g) in sterile purified water, and sterile purified water was further added to give 1000 ml of a solution. This solution was filtered through a 0.22 um membrane filter to form a 0.1% (W/V) solution of AS-152. This solution was filled in an eye drop container to produce an eye drop.

What is claimed is:

1. An aqueous preparation comprising of 0.1 to 0.3% (W/V) of a pyrido[1,2-a]pyrimidine compound represented by the following formula:

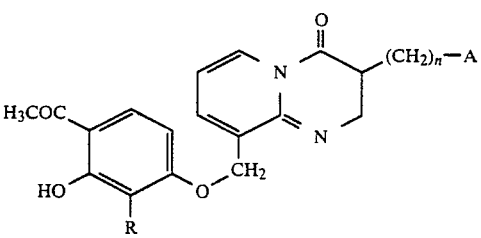

wherein R represents an n-propyl or allyl group, A represents a tetrazolyl or carboxyl group, and n represents an integer of 0 to 2;
0.5 to 2.0% (W/V) of a polyoxyethylene sorbitan fatty acid ester, 0.5 to 2.0% (W/V) of polyethylene glycol and 1.0 to 3.5% (W/V) of disodium hydrogenphosphate.

2. The aqueous preparation of claim 1 in which the polyoxyethylene sorbitan fatty acid ester is polyoxyethylene sorbitan monopalmitate, polyoxyethylene sorbitan monostearate, polyoxyethylene sorbitan tristearate or polyoxyethylene sorbitan monooleate.

3. The aqueous preparation of claim 1 or 2 in which the polyethylene glycol is polyethylene glycol having a molecular weight of 200, polyethylene glycol having a molecular weight of 300, polyethylene glycol having a molecular weight of 400, polyethylene glycol having a molecular weight of 600, polyethylene glycol having a molecular weight of 1000, polyethylene glycol having a molecular weight of 1500, polyethylene glycol having a molecular weight of 1540, polyethylene glycol having a molecular weight of 4000, polyethylene glycol having a molecular weight of 6000, polyethylene glycol having a molecular weight of 20000.

4. The aqueous preparation of claim 3 in which the pyrido[1,2-a]pyrimidine compound is 9-[(4-acetyl-3-hydroxy-2-n-propylphenoxy)methyl]-3-(1H-tetrazo-5-yl)-4H-pyrido[1,2-a]pyrimidin-4-one,
 9-[(4-acetyl-3-hydroxy-2-n-propylphenoxy)methyl]-3-[2-(1H-tetrazol-5-yl)ethyl]-4H-pyrido[1,2-a]pyrimidin-4-one,
 9-[(4-acetyl-3-hydroxy-2-n-propylphenoxy)methyl]-3-[(1H-tetrazol-5-yl)methyl]-4H-pyrido[1,2-a]pyrimidin-4-one, or
 9-[(4-acetyl-3-hydroxy-2-allylphenoxy)methyl]-3-(1H-tetrazol-5-yl)-4H-pyrido[1,2-a]pyrimidin-4-one.

5. The aqueous preparation of claim 3 in which the pyrido[1,2-a]pyrimidine compound is [9-(4-acetyl-3-hydroxy-2-n-propylphenoxymethyl)-4-oxo-pyrido[1,2-a]pyrimidin-3-yl]acetic acid or 3-[9-(4-acetyl-3-hydroxy-2-n-propylphenoxymethyl)-4-oxo-pyrido[1,2-a]pyrimidin-3-yl]propionic acid.

6. The aqueous preparation of claim 3 which is in the form of an eye drop, a nasal drop, or a add skin or mucous membrane paint.

7. The aqueous preparation of claim 1 in which the pyrido[1,2-a]pyrimidine compound is 9-[(4-acetyl-3-hydroxy-2-n-propylphenoxy)methyl]-3-(1H-tetrazol-5-yl)-4H-pyrido[1,2-a]pyrimidin-4-one; the polyoxyethylene sorbitan fatty acid ester is polyoxyethylene sorbitan monooleate; and the polyethylene glycol has a molecular weight of 400.

* * * * *